(12) United States Patent
Martin

(10) Patent No.: US 7,001,018 B1
(45) Date of Patent: Feb. 21, 2006

(54) SURGICAL VISUAL FEEDBACK AND EYE FIXATION METHOD AND APPARATUS

(75) Inventor: Simon Charles Martin, Mt Claremont (AU)

(73) Assignee: Q-Vis Limited, Herdsman (AU)

( * ) Notice: Subject to any disclaimer, the term of this patent is extended or adjusted under 35 U.S.C. 154(b) by 0 days.

(21) Appl. No.: 09/762,824

(22) PCT Filed: Aug. 16, 1999
(Under 37 CFR 1.47)

(86) PCT No.: PCT/AU99/00665

§ 371 (c)(1),
(2), (4) Date: Dec. 26, 2001

(87) PCT Pub. No.: WO00/09002

PCT Pub. Date: Feb. 24, 2000

(30) Foreign Application Priority Data

Aug. 14, 1998 (AU) .......................... PP5284

(51) Int. Cl.
*A61B 3/10* (2006.01)

(52) U.S. Cl. ...................... 351/211; 351/208; 351/209; 606/5; 606/10

(58) Field of Classification Search ................ 606/4–6, 606/10–12; 351/208–212
See application file for complete search history.

(56) References Cited

U.S. PATENT DOCUMENTS

| 3,025,755 A | * | 3/1962 | Koetting ..................... 351/224 |
| 4,536,065 A | | 8/1985 | Sheingorn .................... 351/239 |
| 4,678,297 A | | 7/1987 | Ishikawa et al. ............. 351/208 |
| 4,870,964 A | * | 10/1989 | Bailey et al. ................... 606/6 |
| 4,993,825 A | * | 2/1991 | Abe et al. ..................... 351/210 |
| 5,094,521 A | * | 3/1992 | Jolson et al. ................ 351/210 |
| 5,135,299 A | | 8/1992 | Kitajima et al. ............. 351/205 |
| 5,549,597 A | * | 8/1996 | Shimmick et al. .............. 606/5 |
| 5,784,148 A | | 7/1998 | Peacock |
| 5,841,511 A | * | 11/1998 | D'Souza et al. ............. 351/212 |
| 6,004,313 A | * | 12/1999 | Shimmick et al. .............. 606/5 |
| 6,666,855 B1 | * | 12/2003 | Somani et al. ................. 606/5 |

FOREIGN PATENT DOCUMENTS

| EP | 0164981 | 12/1985 |
| EP | 0 256 635 | 2/1988 |
| WO | 9800078 | 1/1998 |

* cited by examiner

*Primary Examiner*—A. Farah
(74) *Attorney, Agent, or Firm*—Baker Botts LLP

(57) ABSTRACT

A fixation apparatus is provided that limits rotation of the ocular globe of an eye, to facilitate alignment of an instrument with the axis of astigmatism of the eye. The apparatus includes fixation target means (12) for locating in the field of view of the eye so that the eye may fixate on the target. The fixation target means includes or consists of at least one elongate component (16). Also disclosed is a corresponding method, and method and apparatus for supplying visual feedback to an operator during refractive surgery of an eye of a patient.

22 Claims, 2 Drawing Sheets

SURGICAL VISUAL FEEDBACK AND EYE FIXATION METHOD AND APPARATUS

FIELD OF THE INVENTION

The present invention relates, in different aspects, to eye fixation and to the provision of visual feedback to a surgeon, during the delivery of medical laser procedures, particularly in the fields of ophthalmic surgical procedures, such as Photorefractive Keratectomy (PRK) and Laser-in-situ Keratomileusis (LASIK), or any laser based refractive correction. The invention will be described with reference to these applications, though it is to be understood that other applications are envisaged.

BACKGROUND ART

Most existing refractive laser delivery systems provide little feedback for the operator (typically a surgeon). Usually a crosshair graticule is superimposed through the microscope optics to help the operator aim the laser beam correctly onto the cornea. A fixation target or light, such as a flashing LED, is used to ensure that the patient's eye remains correctly aligned during the surgery. However, this arrangement does not necessarily provide the best alignment of the eye and the laser beam, nor does it provide visual feedback for the operator concerning the status of the eye or the laser. It may at times be necessary for the operator to move his or her attention away from the surgical field to check on instrumentation, such as the microkeratome or the laser source. The axis of astigmatism of the patient's eye is also likely to be misaligned when the patent is supine and fixating on a point of light.

Refractive errors are usually assessed when the patient is seated in an upright position using structured shapes or symbols, such as letters of the alphabet. However, refractive surgery is usually performed with the patient reclining in an operating chair. It has been found that, when a patient lies recumbent, the ocular globe is liable to rotate, altering the position of the axis of astigmatism between 7° and 16° in 25% of cases (Smith, Talamo, Assil & Petashnick, "Comparison of Astigmatic Axis in the Seated and Supine Positions", J. of Refractive & Corneal Surgery 10(6), 615 (1994)). This occurs for two reasons: i) the removal of the reference horizon, and ii) the change from binocular to monocular vision. Focussing on a point of light (the flashing LED), instead of the linear horizon, does not provide a proper point of horizontal or vertical reference. The globe is therefore liable to rotate fractionally, possibly resulting in misalignment of the treatment of the eye's axis of astigmatism. The potential end result is under-treatment of the original astigmatic error or inducement of astigmatism at another axis.

U.S. Pat. No. 5,549,597 describes a method for determining the axis of astigmatism of a patient undergoing refractive surgery, so as to provide real-time alignment information for the surgical procedure. The patient is required to focus on a target such as three sets of three lines of variable line spacing, each set corresponding to a different visual acuity, and then to focus on the best resolved set of lines and rotate the target until the finest line is seen most clearly. This method of determining the axis of astigmatism and aligning the surgical laser is not ideal. The patient is forced to make subjective comparisons at a highly stressful time. In addition, the globe may still rotate after the alignment has been performed, and prior to surgery.

An earlier configuration for determining the axis of astigmatism is described in U.S. Pat. No. 3,785,723, and involves rotation of an opaque disk having multiple small apertures backlit by a light source so as to resemble a set of point light sources arranged in a straight line along the diameter of the disk.

U.S. Pat. No. 5,442,412 discloses a patient responsive eye fixation target for use in ophthalmic procedures in which respective light sources produce a ring of light and a dot of light centred on the same optical axis, but respectively closer to and further from the eye. In response to detection of a quantifiable amount of eye movement, the dot is altered in appearance, eg. by flashing or colour changes, to alert the patient that his or her eye is no longer aligned with the dot and ring.

Corresponding to the patient fixation apparatus is the apparatus used by the surgeon to view and assess the extent of fixation and the alignment of the laser beam. The surgeon views this display when looking down the surgical microscope. Current technology provides a display including a graticule or crosshair. A He-Ne beam is sometimes provided for aiming the surgical beam.

U.S. Pat. No. 4,870,964 provides a head-up display for use with an operating microscope during phaco-emulsification procedures. This apparatus allows the operating surgeon to view information about the status of the patient, the eye and operating equipment, such as vacuum pressure, without removing their gaze from the operating field. It does so by projecting light onto the operating field of the eye and conditioning the reflections from the cornea so that interpretable images may be viewed by the surgeon as they look down the microscope. U.S. Pat. No. 5,135,299 describes a similar operating microscope featuring a head-up display, produced by reflecting operational information from the scleral portion of the eye.

It is an object of the present invention, in at least one aspect, to provide an eye fixation method and apparatus that is simple and reliable, and involves minimal expectation of the patient. For particular applications, it is further preferred that the arrangement reduces the angular rotation of the ocular globe to facilitate alignment of an instrument with the axis of astigmatism.

It is an object of another aspect of the present invention to provide a surgical visual feedback method and apparatus that provides increased information to the surgeon or operator.

SUMMARY OF THE INVENTION

According, therefore, to a first aspect of the present invention, there is provided a method for limiting the rotation of the ocular globe of an eye to facilitate alignment of an instrument with the axis of astigmatism of the eye. The method includes providing fixation target means in the field of view of the eye so that the eye may fixate on the target. The fixation target means includes or consists of at least one elongate component having a fixed orientation.

Preferably the method includes providing the fixation target means by way of light emitting means. Preferably, the light emitting means is strobed.

The present invention also provides, in its first aspect, a fixation apparatus that limits rotation of the ocular globe of an eye, to facilitate alignment of an instrument with the axis of astigmatism of the eye. The apparatus includes fixation target means for locating in the field of view of the eye so that the eye may fixate on the target. The fixation target means includes or consists of at least one elongate component having a fixed orientation.

Preferably, said fixation target means includes or consists of at least two intersecting substantially mutually perpendicular elongate components. The fixation target means may consist substantially of a cross, and/or it may include more than two elongate components arranged as a grid. The fixation target means preferably has a fixed orientation.

The fixation target means may be a light emitting means. Moreover, the or each elongate component may be defined by the light emitting means.

Preferably, the light emitting means includes a plurality of light emitting diodes (LEDs) arranged in a respective linear array to define the or each elongate component.

Preferably the apparatus includes a printed circuit board (PCB) on which the LEDs are mounted.

Preferably the apparatus is controllable to strobe the light emitting means.

The apparatus may include a pulsable power supply to strobe the light emitting means.

In its first aspect, the invention extends to laser surgery apparatus incorporating patient observable fixation apparatus as described above.

In a second aspect of the present invention there is provided a method for supplying visual feedback to an operator during refractive surgery of an eye of a patient, including:
1) providing fixation target means for the eye to fixate upon;
2) locating the eye for viewing by viewing means while it is fixated upon said fixation target means;
3) generating an information display of information pertinent to said surgery and suitable for displaying visually; and
4) transmitting the information display to the viewing means for viewing by the operator;
whereby the eye and the information display may be viewed simultaneously by the operator.

Preferably the method includes updating the information display.

Preferably step 3) includes generating the information display with a controller means.

Preferably the controller means is a computer.

Preferably the method includes transmitting the information display to a display means and displaying the information display on the display means.

The display means may be miniature TV or LCD screen or a plurality of LEDs.

Preferably step 1) includes the alignment facilitating method according to the first aspect of the invention.

Preferably the viewing means includes left and right optics means, and the target is located between the left and right optics means.

Preferably the viewing means is a surgical microscope.

The invention extends to a method of performing refractive surgery on an eye of a patient, wherein visual feedback is supplied in accordance with the method of the second aspect of the invention. The refractive surgery may eg. be PRK or LASIK, thermal keratoplasty, intrastromal ablation or any other surgical method that alters the refraction of the eye.

The method may be performed with any laser suitable for use in surgery that involves altering the refractive properties of the eye, e.g. an ultraviolet ablation laser, a Holmium laser, or an Erbium laser at 3 microns.

Preferably step 4) includes viewing said information by means of a beam splitter or plate of glass.

In its second aspect, the invention also provides an apparatus for supplying visual feedback to an operator during refractive surgery of an eye. The apparatus includes fixation target means for the eye to fixate upon, and viewing means for viewing the eye while it is fixated upon the fixation target means. Controller means is provided for generating an information display, and screen means displays the said information display, for viewing by the viewing means, whereby the eye and the information display may be viewed simultaneously by the operator.

Preferably the apparatus includes display means for displaying the information display.

The apparatus may be provided in combination with a surgical laser and thereby comprise laser surgery apparatus.

The laser may be any laser suitable for use in surgery that involves altering the refractive properties of the eye, such as a ultraviolet ablation laser, a Holmium laser, an Erbium laser at 3 microns or any other appropriate laser source.

Preferably the target means is a fixation apparatus according to the first aspect of the invention.

The display means and/or screen means may be viewed by means of a beam splitter or plate of glass.

Preferably the display means is a miniature TV or LCD screen or a plurality of LEDs.

Preferably the viewing means is a surgical microscope.

Preferably the controller means is a computer.

Preferably the viewing means includes left and right optics, and the target is located between the left and right optics.

In the method and apparatus of the second aspect of the invention, the information may include an alert signal indicating misalignment of the patient's eye, eg. due to straying from fixation upon the fixation target means.

The information may pertain to one or more of: the status of the patient, the surgery or the equipment, the position of the eye or where an eye-tracker is aiming the laser.

The information may include one or more of the following elements of operational information: type of treatment, number of laser pulses required to finish, operation time remaining, patient identification and which eye is being treated, keratometry information, refraction information, and/or topographical information.

The information may include microkeratome status information, such as suction and blade speed readings.

BRIEF DESCRIPTION OF THE DRAWINGS

In order that the invention be more fully understood, preferred embodiments will now be described, by way of example, with reference to the accompanying drawings, in which.

PREFERRED EMBODIMENTS

Figure 1:
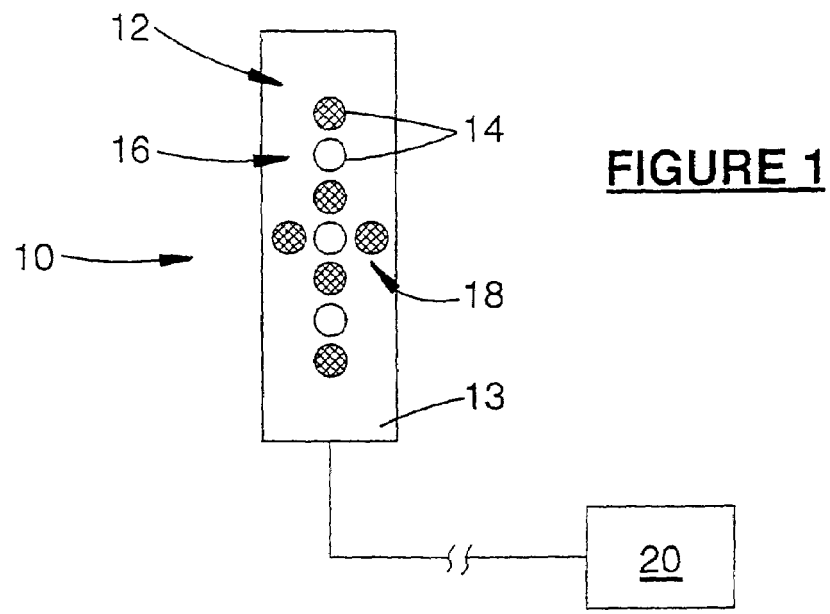
FIG. 1 is a schematic view of an eye fixation apparatus according to a preferred embodiment of the first aspect of the present invention.
Figure 2:
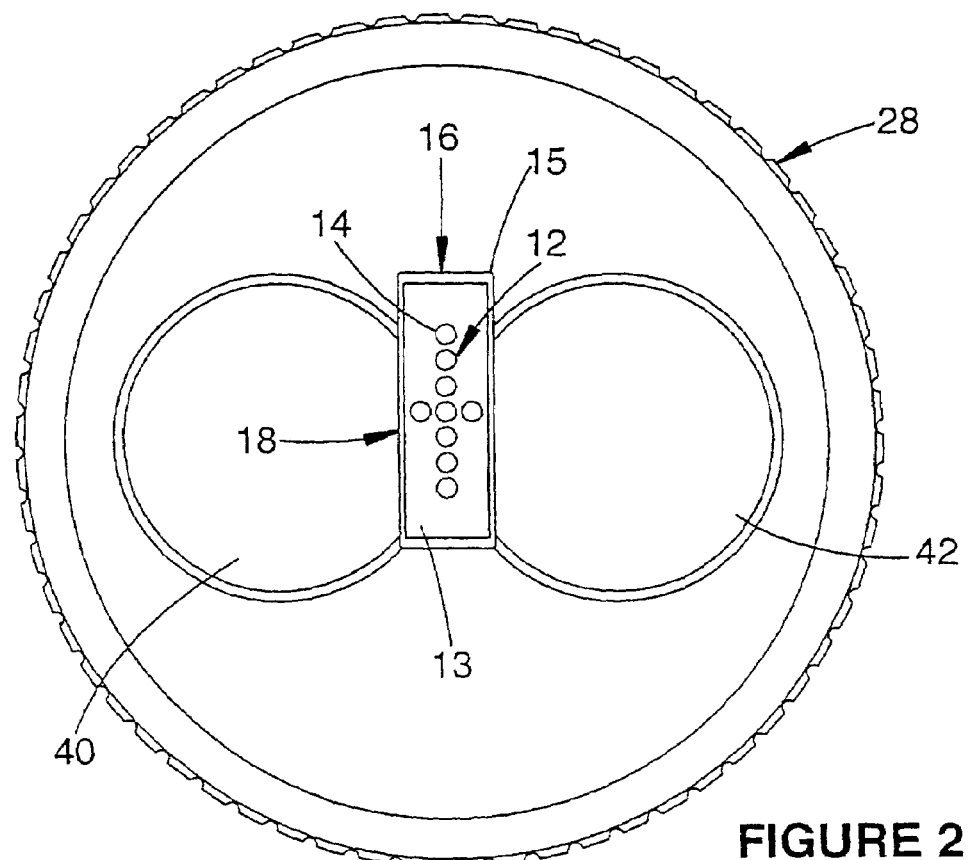
FIG. 2 is a fragmentary view illustrating a suitable location for the eye fixation target.

Referring to FIGS. 1 and 2, there is presented a schematic view of a patient's eye fixation apparatus 10 according to a preferred embodiment of the present invention. The apparatus 10 includes a fixation target in the form of a cross 12 formed by surface mounted light emitting diodes, LEDs 14, arranged in two linear arrays to define intersecting elongate components or axes 16, 18 perpendicular to one another. The LEDs are fixed to a printed circuit board (PCB) 13, in turn arranged on an elongate lipped substrate 15. Substrate 15 is positioned on the front of the surgical microscope 28, symmetrically between the adjacent stereo oculars 40,42, so as to be clearly observable by the patient. Alternatively, cross 12 may be located elsewhere within the surgical laser, and projected to optically appear as if it is placed between the oculars of the microscope.

Substrate 15 is fixed in position on the microscope so that cross 12 has a fixed orientation. "Vertical" axis 16 of the cross 12 of LEDs 14 is longer than "horizontal" axis 18, by providing several more LEDs 14 in axis 16 than axis 18. By "vertical" is meant the axis that extends normal to the lines joining the oculars. The LEDs 14 may alternatively be positioned to form any other pattern of elongate or linear elements, such as a line or a grid.

The cruciform arrangement of LEDs 14 allows the patient to better judge horizontal and vertical directions, so that the ocular globe(s) of the patient does not rotate and the axis of astigmatism is naturally aligned.

A suitable control circuit 20, of a simple form readily apparent to those skilled in the art, is provided for strobing LEDs 14 in a pre-selected, perhaps adjustable, sequence. The LEDs may, for example, flash in unison or in a more complex pattern. LEDs 14 may be of varying colours to facilitate patient concentration and gaze control. In use, the patient is required to fixate his or her gaze on the flashing cross 12, thereby preventing angular rotation of the ocular globe and misalignment of the treatment eye's axis of astigmatism. A preferred flash rate is about 1.5 Hz with a duty cycle of about 50%. The duty cycle may be adjustable, for example to allow more light during LASIK and less light during PRK.

Figure 3:
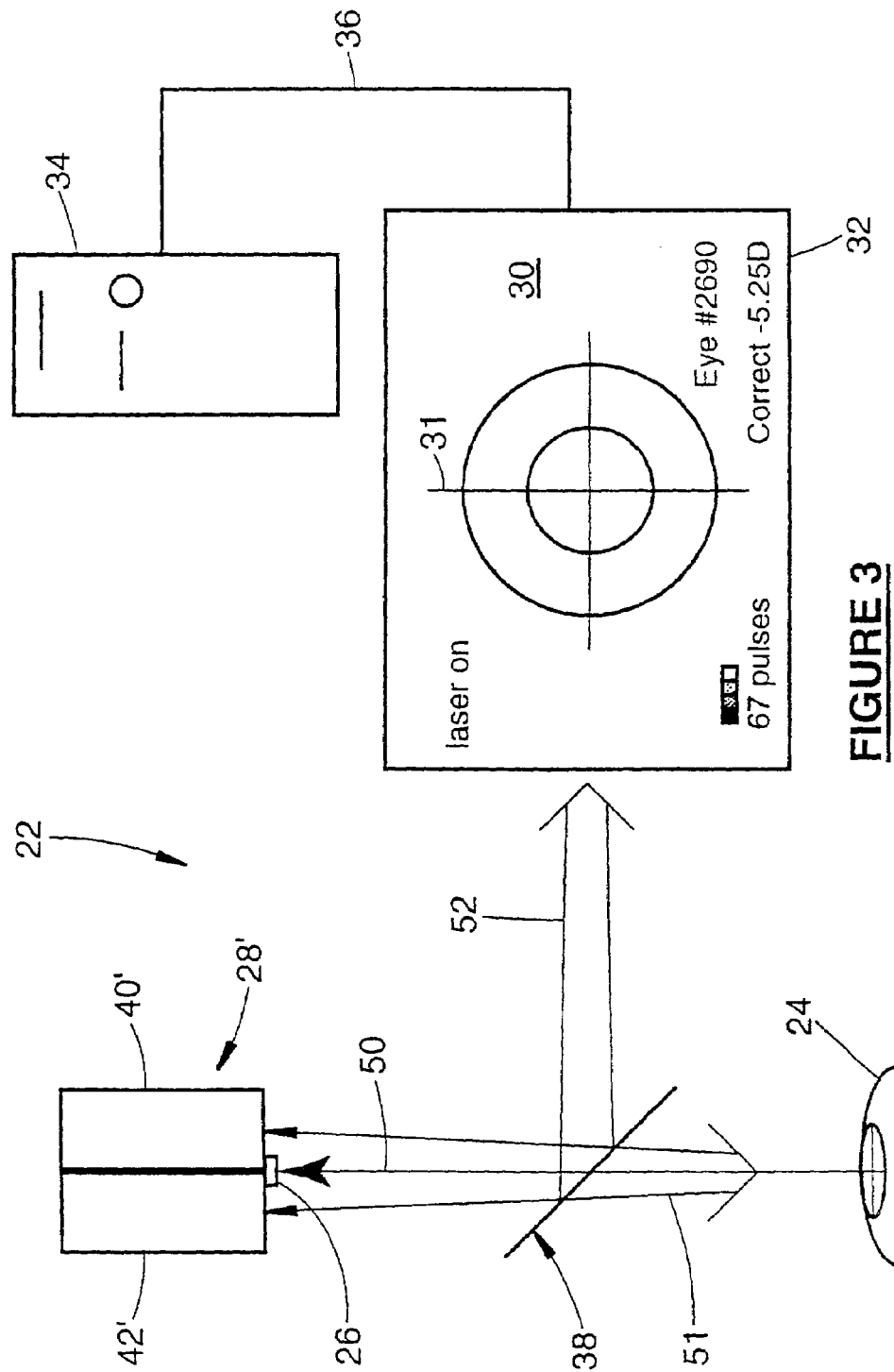
FIG. 3 is a diagram of the layout of the principal components of an arrangement for supplying visual feedback to an ophthalmic surgeon during refractive laser eye surgery procedures, according to a preferred embodiment of the second aspect of the present invention, but preferably incorporating the embodiment of FIGS. 1 and 2.

FIG. 3 is a diagram of an apparatus 22 for supplying visual feedback to an ophthalmic surgeon during refractive laser eye surgery procedures being performed on an eye 24. This apparatus is an embodiment of the second aspect of the invention. The apparatus 22 includes a surgical microscope 28', a fixation target 26, which is preferably a flashing cross 12' as in FIGS. 1 and 2, on microscope 28', a head-up display 30 to give the surgeon feedback regarding patient fixation, the operating conditions and other pertinent information, and an imaging device in the form of a miniaturised TV or LCD screen 32 supplied within the laser delivery head (not shown). The head-up display 30 may be produced by projecting lights onto a surface, as is known in the art, and may be displayed on screen 32. The imaging device may alternatively comprise a combination of light emitting diodes.

The apparatus 22 further includes a controller in the form of computer 34 and; communications link 36 between computer 34 and screen 32. Computer 34 generates the information content (comprising information pertinent to the operation being carried out) of the head-up display 30, and transmits this content via link 36 to screen 32 to display. This content could include a pulse countdown, operation time remaining, an alert signal indicating misalignment of the patient's eye, a cross 31 indicating where the laser is currently aimed, patient information such as name or ID, treatment zone information, topographical information and any other information that the surgeon may deem useful.

The apparatus 22 also includes a beamsplitter 38, by which the head-up display 30 is viewed. The beamsplitter 38 forms a part of the optics of the laser (not shown), for relaying this information towards oculars 40', 42' of the microscope 28', so that the operator may see the information when he or she looks down the microscope 28'.

Thus, in use, while the patient views (50) a suitable fixation target 26 (such as a fixation cross 12' as described above), the surgeon is able to view the patient's eye 24 (51) and the head-up display 30 (52) through the surgical microscope 28'.

The invention claimed is:

1. In refractive laser surgery apparatus, a fixation apparatus for limiting rotation of an ocular globe of an eye of a patient during refractive laser surgery on the eye, to facilitate alignment of the surgery apparatus with an axis of astigmatism of the eye, comprising:

fixation target means disposed at a patient observable position in a field of view of said eye so that said eye may fixate on said target;

wherein said target means comprises light emitting means that when activated defines at least two intersecting, substantially mutually perpendicular elongate components, each having a location and orientation that remains fixed during said surgery on the eye, thereby limiting rotation of the ocular globe of the patient's eye during said surgery.

2. Apparatus according to claim 1 wherein said fixation target means includes at least two intersecting components.

3. Apparatus according to claim 1 wherein said fixation target means consists substantially of a cross.

4. Apparatus according to claim 1 wherein one of the at least two elongate components is longer than the other.

5. Apparatus according to claim 1 wherein said fixation target means includes more than two elongate components arranged as a grid.

6. Apparatus according to claim 1 wherein said fixation target means is a light emitting means.

7. Apparatus according to claim 6 wherein the or each said elongate component is defined by said light emitting means.

8. Apparatus according to claim 6, further including means to strobe said light emitting means.

9. Apparatus according to claim 1, wherein said light emitting means includes a plurality of light emitting diodes arranged in a respective linear array to define the or each said elongate component.

10. Apparatus according to claim 9, further including a printed circuit board (PCB) on which the light emitting diodes are mounted.

11. Laser surgery apparatus incorporating patient observable fixation apparatus according to claim 1.

12. Laser surgery apparatus according to claim 1, wherein said fixation target means is disposed in a patient observable position on a surgical microscope of said laser surgery apparatus.

13. Laser surgery apparatus according to claim 12 wherein said at least one elongate component is arranged in a "vertical" orientation on said surgical microscope.

14. An apparatus according to claim 1, wherein said fixation target means has a fixed orientation.

15. In refractive laser surgery on an eye of a patient, a method for limiting rotation of an ocular globe of said eye during said surgery, to facilitate alignment of surgery apparatus with an axis of astigmatism of the eye, comprising providing fixation target means at a patient observable position in the field of view of said eye so that said eye may fixate on said target, wherein said fixation target means comprises activated light emitting means that defines at least two intersecting substantially mutually perpendicular elongate components each having a location and orientation that remains fixed during said surgery on the eye, thereby limiting rotation of the ocular globe of the patient's eye during said surgery.

16. A method according to claim 15, wherein said fixation target means includes or consists of at least two intersecting, substantially mutually perpendicular elongate components.

17. A method according to claim 15, wherein said fixation target means consists substantially of a cross.

18. A method according to claim 15, wherein said fixation target means includes more than two components arranged as a grid.

19. A method according to claim 15, including providing said fixation target means by way of light emitting means.

20. A method according to claim 15, wherein said light emitting means includes a plurality of light emitting diodes arranged in a respective linear array to define the or each said elongate component.

21. A method according to claim 15, further including strobing of said light emitting means.

22. A method according to claim 15, wherein said fixation target means is provided so as to have a fixed orientation.

* * * * *

UNITED STATES PATENT AND TRADEMARK OFFICE
CERTIFICATE OF CORRECTION

PATENT NO. : 7,001,018 B1
DATED : February 21, 2006
INVENTOR(S) : Saarloos et al.

It is certified that error appears in the above-identified patent and that said Letters Patent is hereby corrected as shown below:

<u>Title page,</u>
Item [75], Inventors, "Simon Charles Martin, Mt. Claremont (AU)." should read
-- Paul Phillip Van Saarloos, Karrinyup (AU); Jon Dishler, (Engelwood, CO). --.

Signed and Sealed this

Thirtieth Day of May, 2006

JON W. DUDAS
*Director of the United States Patent and Trademark Office*